US006529612B1

(12) United States Patent
Gester et al.

(10) Patent No.: US 6,529,612 B1
(45) Date of Patent: Mar. 4, 2003

(54) METHOD FOR ACQUIRING, STORING AND ANALYZING CRYSTAL IMAGES

(75) Inventors: Thomas E. Gester, Mountain Brook, AL (US); William M. Rosenblum, Birmingham, AL (US); Gayle K. Christopher, Harpersville, AL (US); David T. Hamrick, Glencoe, AL (US); Lawrence J. Delucas, Birmingham, AL (US); Brian Tillotson, Kent Washington, WA (US)

(73) Assignee: Diversified Scientific, Inc., Birmingham, AL (US)

( * ) Notice: Subject to any disclaimer, the term of this patent is extended or adjusted under 35 U.S.C. 154(b) by 0 days.

(21) Appl. No.: 09/462,950
(22) PCT Filed: Jul. 16, 1998
(86) PCT No.: PCT/US98/14776
§ 371 (c)(1),
(2), (4) Date: Jun. 1, 2000
(87) PCT Pub. No.: WO99/04361
PCT Pub. Date: Jan. 28, 1999

Related U.S. Application Data

(60) Provisional application No. 60/052,902, filed on Jul. 16, 1997.

(51) Int. Cl.[7] ................................................ G06K 9/00
(52) U.S. Cl. ...................................................... 382/100
(58) Field of Search ............................... 382/100, 108, 382/109; 356/30

(56) References Cited

U.S. PATENT DOCUMENTS

| 4,900,147 A | * | 2/1990 | Bowley et al. | ................ 356/30 |
| 5,076,698 A | * | 12/1991 | Smith et al. | ................. 356/376 |
| 5,124,935 A | * | 6/1992 | Wallner et al. | ............. 364/525 |
| 5,193,685 A | * | 3/1993 | Trevithick | .................. 209/3.1 |
| 5,544,254 A | * | 8/1996 | Hartley et al. | .............. 382/108 |

* cited by examiner

Primary Examiner—Andrew W. Johns
(74) Attorney, Agent, or Firm—Gifford, Krass, Groh, Sprinkle, Anderson & Citkowski, P.C.

(57) ABSTRACT

A system utilizing a digital computer for acquiring, storing and evaluating crystal images. The system includes a video camera (12) which produces a digital output signal representative of a crystal specimen positioned within its focal window (16). The digitized output from the camera (12) is then stored on data storage media (32) together with other parameters inputted by a technician and relevant to the crystal specimen. Preferably, the digitized images are stored on removable media (32) while the parameters for different crystal specimens are maintained in a database (40) with indices to the digitized optical images on the other data storage media (32). Computer software is then utilized to identify not only the presence and number of crystals and the edges of the crystal specimens from the optical image, but to also rate the crystal specimens by various parameters, such as edge straightness, polygon formation, aspect ratio, surface clarity, crystal cracks and other defects or lack thereof, and other parameters relevant to the quality of the crystals.

9 Claims, 3 Drawing Sheets

METHOD FOR ACQUIRING, STORING AND ANALYZING CRYSTAL IMAGES

This application claims benefit of Prov. Appl. No. 60/052,902 filed Jul. 16, 1997.

This invention was made with Government support under contract NAS8-40839 awarded by NASA. The Government has certain rights in this invention.

BACKGROUND OF THE INVENTION

I. Field of the Invention

The present invention relates to a computer controlled system which acquires, stores and analyzes crystal images and other parameters relevant to the crystals, or microscopic details of other specimens.

II. Description of the Prior Art

In many chemical, pharmaceutical and medical applications crystals, e.g. protein crystals, are grown in trays for subsequent evaluation by a lab technician or scientist (hereinafter collectively referred to as "technician"). In evaluating the crystals once grown, the lab technician examines the crystals under the microscope and then visually evaluates or rates individual crystals. The straightness of the crystal edges, size of the crystal, presence or absence of flaws in the crystal as well as other crystal parameters are used by the technician in his or her rating process. The technician may also maintain notes of other parameters, such as pH, crystal growing time, temperature, et cetera, which are relevant to the particular crystal.

In some instances, the technician will take and maintain a photograph of the particular crystal under examination. The photograph is then stored along with the notes relevant to the particular crystals in the particular tray.

This previously known system for evaluating and rating crystals is disadvantageous for a number of reasons. Most prominently, the crystal evaluation and rating system is labor intensive and, thus, not only slow and expensive in labor costs, but also tedious for the technician.

A still further disadvantage of these previously known systems is that the photographic record used for the examined crystal is expensive in material costs from the photographic process. Furthermore, photographs by their very nature are easily damaged and also deteriorate over time.

A still further disadvantage of the previously known method for evaluating and rating crystals is that no efficient means or system has been previously known for cross-referencing the various crystals and crystal parameters relative to each other. Instead, the photographic picture as well as the other parameters relevant to the particular picture are simply maintained separately from the crystal specimens.

SUMMARY OF THE PRESENT INVENTION

The present invention provides a system utilizing a digital computer which overcomes all of the above-mentioned disadvantages of acquiring, storing and evaluating crystals, such as protein crystals, or microscopic details of other specimens.

In brief, the present invention utilizes a video camera which provides a digital output signal representative of an object, in this case crystals maintained within a tray, positioned within its focal window. Preferably, a central computer controls a movable stage to sequentially position trays in the focal window. The camera is operated under the control of a central computer which not only activates the initiation of the image acquisition by the camera, but also stores the output from the camera in digital form on data storage media. Preferably, the optical image from the video camera is stored on removable data storage media, such as a JAZZ™ drive, ZIP™ drive or CD ROM, etc.

In addition to storing the acquired optical image from the video camera, the technician, via a computer keyboard, mouse or other computer input means, also inputs data corresponding to parameters relevant to the particular crystal specimen under examination. Such parameters can include, for example, the pH, temperature, duration of crystal growth, et cetera for the particular crystal specimen. Additionally, the computer software preferably provides input template configurations to simplify the data input of the parameters by the technician and thus avoid or at least minimize the redundant input of information for different trays having similar parameters.

The various stored parameters may also be stored with the optical image on the data storage media. However, more preferably, the parameters relevant to the crystal specimens are stored in a database on one data storage media, for example a hard drive, with an index or record pointer to the appropriate image stored on the removable drive with the optical images. In this fashion, a large database of the various crystal parameters may be maintained and analyzed relative to each other with access to the optical images always available as required or desired.

Following acquisition of the optical image as well as the other crystal parameters, the computer is programmed to analyze the optical image for the presence and count of protein crystals. As a part of the evaluation, the computer program identifies the edges of the crystal, filling in any gaps of the edge where necessary, and than analyzes the resulting data for its perimeter symmetry and roughness, straightness, crystal size, presence or absence of defects and center of gravity. The crystal rating is then stored in the data base.

Preferably, the present invention utilizes a fast T-squared filer during its analysis of the optical image in order to grade the crystal. Alternatively, the present invention utilizes a 3×3 edge detection filter during its analysis of the optical image in order to identify the crystal edges, then the image is converted to a binary image with a threshold of approximately 40 on a scale of 0 to 255 to reduce image artifacts. The size of the crystal is determined via perimeter connectivity analysis. Objects with a small perimeter are excluded. The net resulting image is analyzed for its roughness which is a measure of the perimeter divided by the convex perimeter. This metric is used to isolate the crystal from the drop boundary and other artifacts. The center of gravity is calculated on the remaining data to pinpoint the crystals.

Alternatively, other methods may also be used to grade the crystal based upon metrics such as edge straightness, aspect ratio, surface clarity, polygon formation, color etc. These methods include the use of traditional spatial filters such as highpass, lowpass, Butterworth, homomorphic, Sobel, Laplacian, etc. Probabilistic restoration such as least mean square (Wiener) filters, fast T-squared filters, spatial transformations, frequency transformations, etc. can be used. Edge linking and boundary detection using Hough Transforms, "Line-filler" filters, thresholding, etc. can be used. Representation and description using Fourier descriptors, topological descriptors, texture descriptors, statistical descriptors, moments, mathematical morphological descriptors, etc. can be used. Recognition using minimum distance classifiers, correlation classifiers, statistical classifiers, Bayesian classifiers, neural networks, genetic algorithms, etc. can be used.

BRIEF DESCRIPTION OF THE DRAWING

A better understanding of the present invention will be had upon reference to the following detailed description when read in conjunction with the accompanying drawing, wherein like reference characters refer to like parts throughout the several views, and in which.

DETAILED DESCRIPTION OF A PREFERRED EMBODIMENT OF THE PRESENT INVENTION

Figure 1:
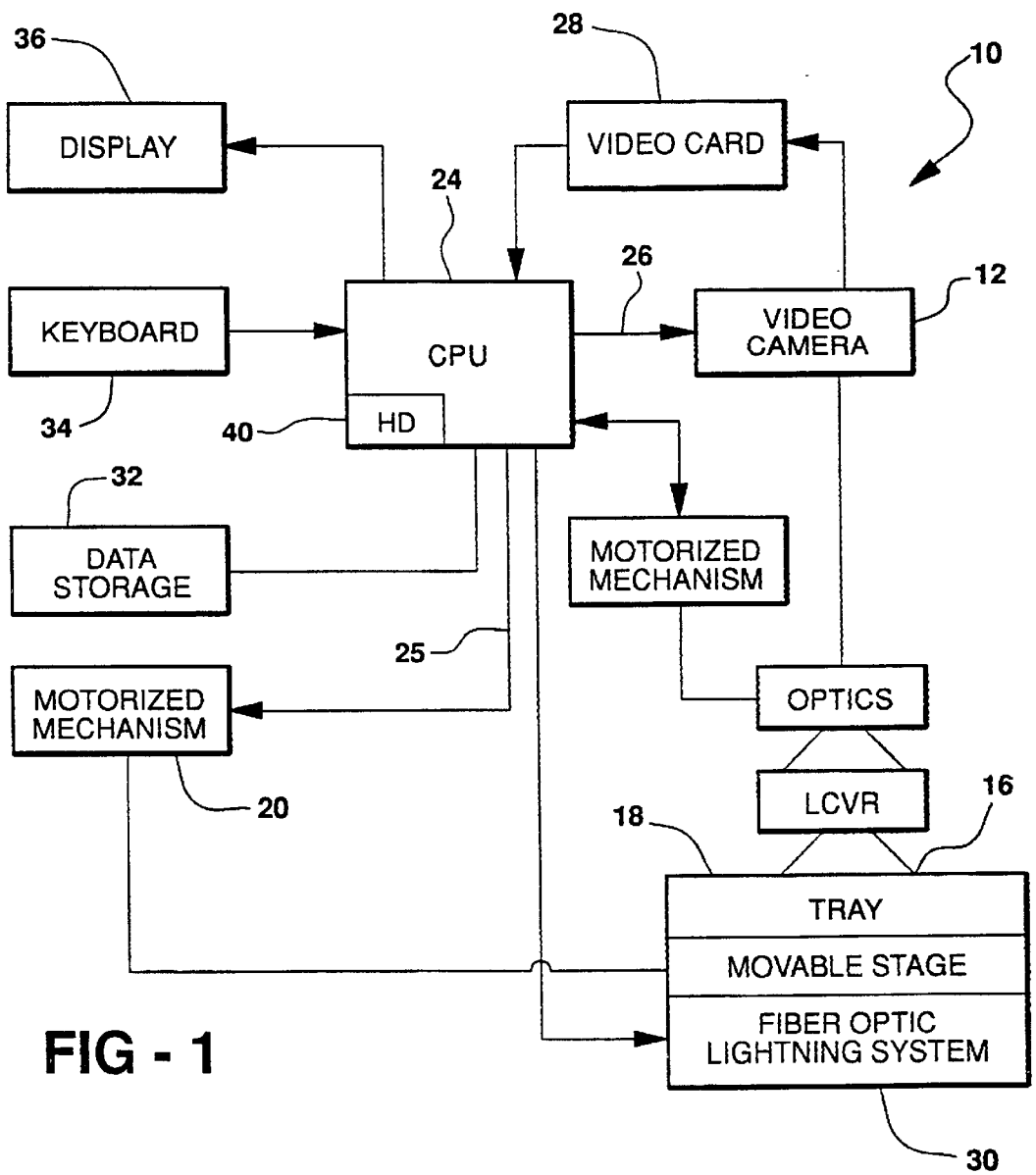
FIG. 1 is a block diagrammatic view illustrating a preferred embodiment of the present invention.

With reference first to FIG. 1, a block diagrammatic view of a preferred embodiment of the system of the present invention is there shown and comprises a video camera 12 which, upon activation, generates a signal on its output line 10 representative of the optical image in its focal window 16. A tray 18 containing the crystals under examination is positioned within the focal window 16.

Although the tray 18 can be positioned manually within the focal window 16 of the camera 12, in the preferred embodiment of the invention, preferably a plurality of trays 18, e.g. two trays, are positioned on a movable stage at a time and each tray contains twenty-four to ninety-six wells while a motorized mechanism 20 is used to control the position of the stage 22. A central processing unit or computer 24, under program control, then controls the activation of the motorized mechanism 20 by generating appropriate signals on line 25 and thus controls the position of the stage 22. In doing so, the motorized mechanism 20 automatically sequentially positions the individual wells 18 within the focal window 16 of the camera 12 so that an optical image of each well 18 is acquired. In one embodiment, the computer 24 can control the ability of the system to focus, as well as zoom in/out on the specimen, and then store this information.

Once the motorized mechanism 20 has positioned a desired well 18 in the focal window 16, the central processing unit 24 generates an output signal on its output line 26 to the camera 12 in order to activate the camera 12 to produce signals on its output line 14 representative of the crystal image. These output signals are fed as input signals to the central processing unit 24 either directly via a port on the central processing unit 24 or via an appropriate input device 28, such as an appropriate video card.

In order to ensure even illumination of the crystal specimen during the image acquisition by the camera 12, preferably a fiber optic lighting system 30 is utilized as a back light under the tray 16. In one embodiment, the computer 24 can control the intensity of the lighting system 30, as well as the presence of light. Additionally, the computer 24 can also control polarizing means, such as the angle of polarization. Other illumination means, however, may alternatively be used.

Following acquisition of the output signal from the video camera 12, the central processing unit 24 stores the image on data storage media using a storage device 32. Since a digital representation of an optical image typically consumes a relatively great amount of memory, e.g. one megabyte, the data storage device 32 is preferably a removable data storage media such as a JAZZ™ drive, ZIP™ drive or CD ROM, etc. Other types of media, including other types of removable data storage media, may alternatively be used.

During the data acquisition of the image by the central processing unit 24, the technician also utilizes a keyboard 34 or other data input equipment together with a video monitor 36 to input data pertinent to the particular crystal specimen. Such data input can include, for example, the pH of the specimen, temperature of the specimen, protein type of the specimen, detergents, additives, preservatives, reservoir buffer and associated variables of concentration, pH and volume, notes, score, drop descriptor, etc. Furthermore, in order to facilitate the entry of these additional parameters by the technician, the central processing unit 24 preferably utilizes software templates displayed on the video monitor 36 to eliminate, or at least minimize, the entry of redundant or repetitive information by the technician.

The various parameters for each crystal specimen are also stored on data storage media, such as a hard drive 40, in a database and preferably in a relational database. Since the various parameters pertinent to the crystal specimens consume considerably less storage space than the optical images themselves, preferably the parameters are stored on the hard drive 40 separate from the optical images stored by the data storage device 32. In doing so, the parameters stored on the hard drive 40 would include an index or pointer to the optical images stored by the data storage media unit 32 so that the various crystal parameters stored in the database may be easily correlated whenever desired to the optical images.

The storage of the optical images of the crystals on data storage media as well as the storage of the crystal parameters in a database, such as a relational database, provide substantial advantages over the previously known photography and handwritten notes currently utilized by technicians. Perhaps most importantly, the use of a relational database allows the data to be analyzed, sorted, correlated and otherwise manipulated under software control by the central processing unit 24. The storage of the optical images on data storage media also provides a permanent record of the images without the previously known degradation and possible damage of photographs.

Figure 2:
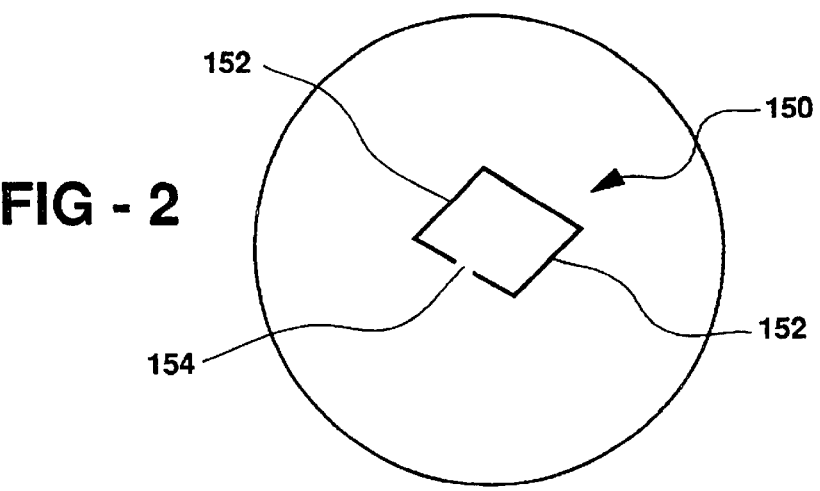
FIG. 2 is an exemplary image of a crystal.

With reference now to FIG. 2, an exemplary image of a crystal stored by the central processing unit on data storage media is there shown. The crystal 150 includes a plurality of edges 152 having a certain degree of straightness. Additionally, the edges 152 of the image of the crystal 150 may include gaps 154 due to lighting deficiencies during the image acquisition, deficiencies of the camera 12, or for other reasons.

Figure 3:
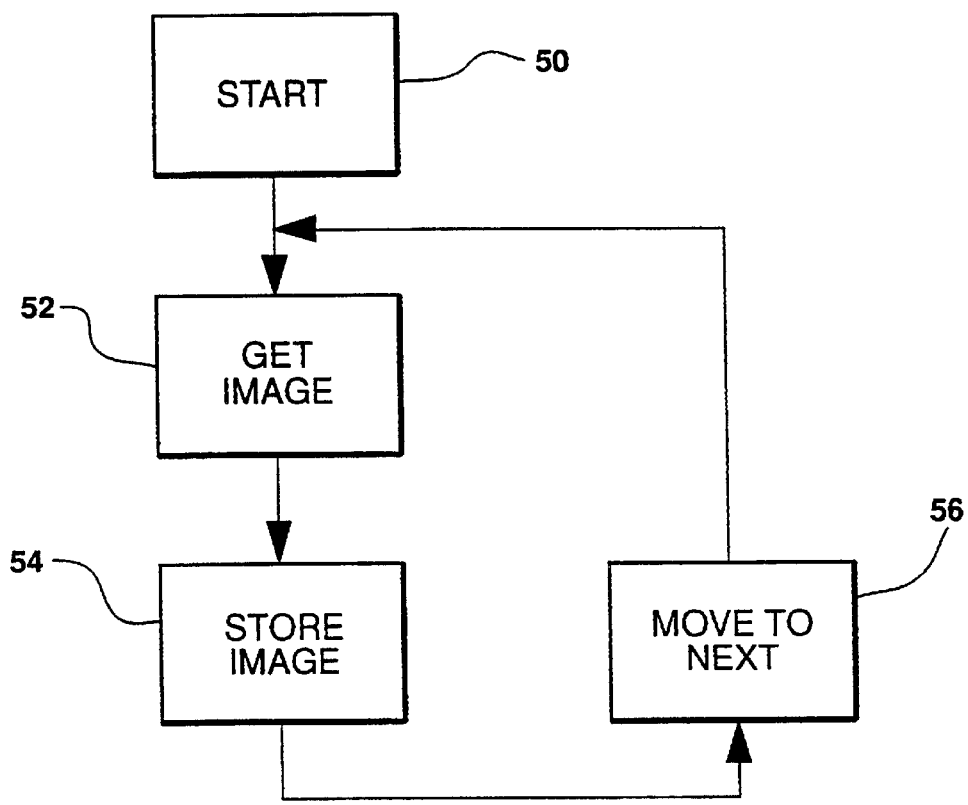
FIGS. 3 through 6 are flow charts illustrating the operation of the system of the present invention.

With reference now to FIG. 3, a flow chart illustrating the operation of the present invention is there shown. At step 50, the program is initialized and the central processing unit 24 generates signals on its output line 25 to the motorized mechanism 20 (FIG. 1) in order to move the stage 22 to position the first crystal tray well 18 within the focal window 16 of the video camera 12. Step 50 then branches to step 52. At step 52, the central processing unit 24 generates an output signal on line 26 to activate the video camera 12 to acquire the optical image and to input the optical image from the camera output line 10 of the camera 12 to the central processing unit 24. Step 52 then branches to step 54.

At step 54, the central processing unit 24 stores the optical image via the data storage device 32 (FIG. 1). Optionally, appropriate data compression software may be utilized to minimize the storage required by the optical image of the crystal storage. Likewise, optionally digital filtering algorithms may be also utilized to remove extraneous noise and otherwise enhance the digital image prior to storage on the data storage media by the storage device 32 or 40.

Concurrently with storing the optical image of the crystal on data storage media, the technician inputs various relevant parameters, such as pH, temperature, crystal growth duration, protein type, et cetera pertinent to the crystal under examination via the keyboard 34 or other input device. Preferably, the central processing unit 24 under software control provides appropriate templates to the technician replicating various parameters common to the various specimens in the trays 18 on the stage 22. In doing so, the entry of redundant or duplicative information by the technician between crystal specimens is minimized which minimizes not only the labor required from the lab technician, but also the entry of errors through human technician error.

The various crystal parameters entered by the technician are also stored at step 54 by the central processing unit 24 on the data storage media 32 or 40 (FIG. 1). Stored concurrently with the crystal parameters on the data storage media 32 or 40 is an index or pointer which correlates the stored crystal parameters to the stored image on data storage media by the data storage device 32.

Step 54 then branches to step 56 whereupon the central processing unit 24 generates output signals on its output line 25 to activate the motorized staged mechanism 20 to move the stage 22 to position the next well in the focal window 16 of the camera 12. Step 56 then branches to step 52 where steps 52 and 54 are reiteratively executed until an optical image and crystal parameters for each of the wells 18 on the stage 22 have been acquired and stored as previously described.

Figure 4:
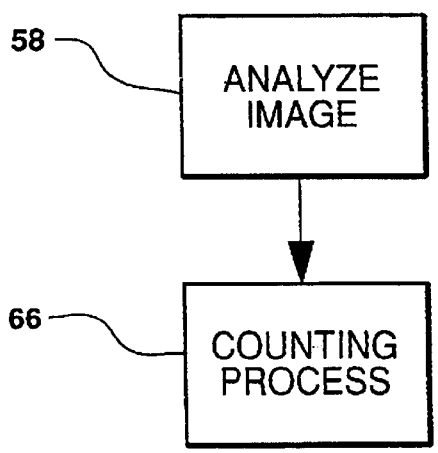
Figure 5:
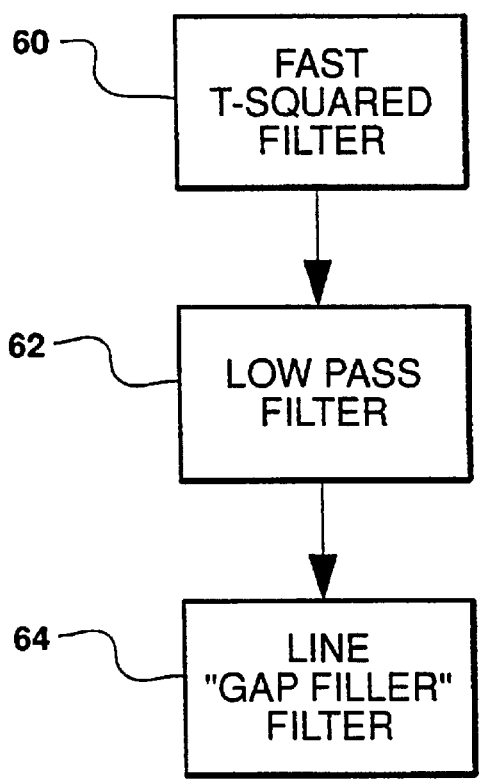

With reference now to FIGS. 4 and 5, following the acquisition and storage of the images and crystal parameters, step 58 is then executed to analyze the stored image. Step 58 is illustrated in greater detail in FIG. 5 and FIG. 6.

With reference then to FIG. 5, during the analysis of the stored image, the program at step 60 executes a fast T-squared filter in order to locate and identify the edges of the crystal image. The fast T-squared filter is essentially a local digital filter which looks for a line defined as a set of co-linear pixels having a mean value different from the mean value of adjacent pixels on both sides of the line. Preferably, the fast T-squared filter at step 60 computes the two sample T-statistic with a null value of 0.

Preferably, the T-squared filter utilizes integer mathematics to minimize computing time required by the central processing unit. The T-squared filter at step 60 is also preferably a variable width T-filter which identifies lines having variable widths, e.g. a width varying in size from one pixel to five pixels. Step 60 then branches to step 62.

At step 62 a low pass filter is applied to the image to remove extraneous noise. Step 62 then branches to step 64.

At step 64, the program "fills" digitally any gaps, such as the gap 54 in FIG. 2, which may be present in the digitized image. Thus, following step 64, the program has identified not only the lines of the crystal, but also eliminated extraneous noise in the crystal image as well as completed any missing segments of the crystal edges due to deficiency of the camera, lighting or the like. Step 64 then branches to step 66 (FIG. 4).

At step 66, the program "scores" or evaluates the crystal images and then stores the score or evaluation as one of the crystal parameters on the storage device 40. Such scoring includes examination and evaluation of the straightness of the crystal edges, the presence or absence of defects in the crystal, fractures in the crystal and the like.

Figure 6:
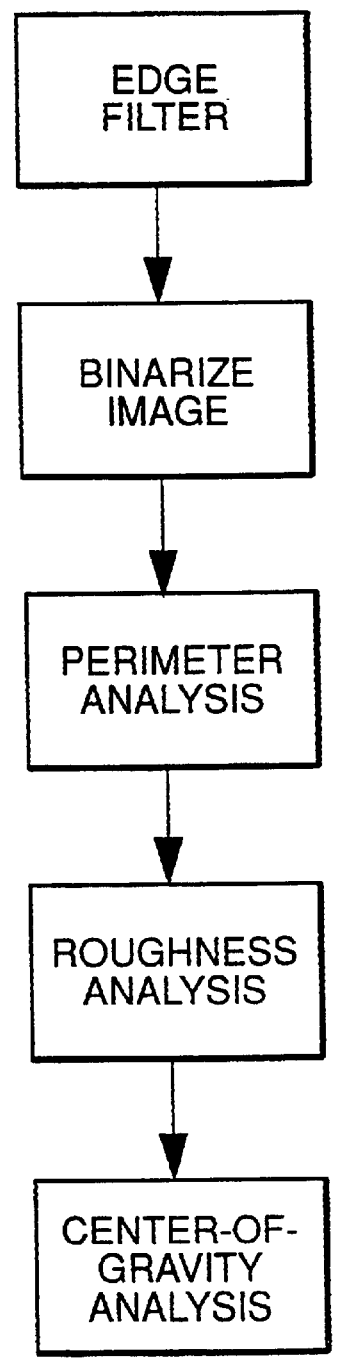

With reference then to FIG. 6, during the analysis of the stored image, the computer is programmed to analyze the optical image for the presence and count of protein crystals. As a part of the evaluation, the computer program identifies the edges of the crystal and than analyzes the resulting data for its perimeter symmetry and roughness and center of gravity.

Preferably, the present invention utilizes a 3×3 edge detection filter during its analysis of the optical image in order to identify the crystal edges, then the image is converted to a binary image with a threshold of approximately 40 on a scale of 0 to 255 to reduce image artifacts. The size of the crystal is determined via perimeter connectivity analysis. Objects with a small perimeter are excluded. The net resulting image is analyzed for its roughness which is a measure of the perimeter divided by the convex perimeter. This metric is used to isolate the crystal from the drop boundary and other artifacts. The center of gravity is calculated on the remaining data to pinpoint the crystals.

From the foregoing, it can be seen that the present invention provides a system for the automatic acquisition, storage and evaluation of crystal specimens under computer control. The use of software templates by the operator to minimize the entry of duplicative or repetitive information further enhances not only the reliability of the data inputted into the system, but also minimizes technician labor.

A still further advantage of the present invention is the storage of the crystal parameters in a relational database which enables the manipulation and evaluation (i.e., experimental history, archiving, trend analysis, etc.) of the crystal parameters under computer control utilizing search and 3-D plotting capabilities. The storage of the crystal images in removable data storage media separate from the storage of the crystal parameters also ensures that a large number of crystal parameters can be stored in the relational database with access to the crystal images always available.

Having described our invention, however, many modifications thereto will be come apparent to those skilled in the art to which it pertains without deviation from the spirit of the invention as defined by the scope of the appended claims.

We claim:

1. A system for utilizing a digital computer to evaluate microscopic details of at least one crystal, comprising:
    a camera which generates an output signal representative of an image positioned in a focal plane of the camera,
    a tray which positions said at least one crystal in said focal plane,
    a computer processing unit having a persistent storage device, which computer processing unit acquires said output signal from said camera,
    said computer processing unit being programmed to evaluate said stored image from said camera and for generating a result signal representative thereof,
    said computer processing unit being programmed to store said result signals in said persistent storage device and performing at least one function selected from the group consisting of: to count crystals, to generate three-dimensional surface plots of crystals within a database, and to determine crystal size by determination of the length of the perimeter of said crystals.

2. The invention as defined in claim 1 and comprising a movable stage for automatically positioning said at least one crystal in said focal plane.

3. The invention as defined in claim 1 wherein data relating to said at least one crystal is stored in the database.

4. The invention as defined in claim 1 and comprising a computer algorithm executed by said computer processing unit for rating said at least one crystal with respect to predetermined standards.

5. A system for utilizing a digital computer to evaluate microscopic details of at least one crystal, comprising:

a camera which generates an output signal representative of an image positioned in a focal plane of the camera, a tray which positions said at least one crystal in said focal plane, a computer processing unit having a persistent storage device, which computer processing unit acquires said output signal from said camera, said computer processing unit being programmed to evaluate said stored image from said camera and for generating a result signal representative thereof, said computer processing unit being programmed to store said result signals in said persistent storage device, and a T-squared filter to identify said at least one crystal.

6. The invention as defined in claim 5 where said T-squared filter comprises a software program executed by said computer processing unit.

7. The invention as defined in claim 2 wherein said computer processing unit generates output signals to control the movement of said movable stage.

8. A system for utilizing a digital computer to evaluate microscopic details of at least one crystal, comprising:

a camera which generates an output signal representative of an image positioned in a focal plane of the camera, a tray which positions said at least one crystal in said focal plane, a computer processing unit having a persistent storage device, which computer processing unit acquires said output signal from said camera, said computer processing unit being programmed to evaluate said stored image from said camera and for generating a result signal representative thereof, said computer processing unit being programmed to store said result signals in said persistent storage device, and an optical fiber extending between a light source directed onto said at least one crystal and said at least one crystal.

9. A system for utilizing a digital computer to evaluate microscopic details of at least one crystal, comprising:

a camera which generates an output signal representative of an image positioned in a focal plane of the camera, a tray which positions said at least one crystal in said focal plane, a computer processing unit having a persistent storage device, which computer processing unit acquires said output signal from said camera, said computer processing unit being programmed to evaluate said stored image from said camera and for generating a result signal representative thereof, said computer processing unit being programmed to store said result signals in said persistent storage device, and a computer algorithm executed by said computer processing unit for simulating edges of crystals missing in said image generated by said camera.

* * * * *

US006529612C1

(12) EX PARTE REEXAMINATION CERTIFICATE (5363rd)
United States Patent
Gester et al.

(10) Number: US 6,529,612 C1
(45) Certificate Issued: May 2, 2006

(54) METHOD FOR ACQUIRING, STORING AND ANALYZING CRYSTAL IMAGES

(75) Inventors: Thomas E. Gester, Mountain Brook, AL (US); William M. Rosenblum, Birmingham, AL (US); Gayle K. Christopher, Harpersville, AL (US); David T. Hamrick, Glencoe, AL (US); Lawrence J. Delucas, Birmingham, AL (US); Brian Tillotson, Kent, WA (US)

(73) Assignee: Diversified Scientific, Inc., Birmingham, AL (US)

Reexamination Request:
No. 90/006,967, Mar. 12, 2004

Reexamination Certificate for:
Patent No.: 6,529,612
Issued: Mar. 4, 2003
Appl. No.: 09/462,950
Filed: Jun. 1, 2000

(22) PCT Filed: Jul. 16, 1998
(86) PCT No.: PCT/US98/14776
§ 371 (c)(1), (2), (4) Date: Jun. 1, 2000
(87) PCT Pub. No.: WO99/04361
PCT Pub. Date: Jan. 28, 1999

Related U.S. Application Data
(60) Provisional application No. 60/052,902, filed on Jul. 16, 1997.

(51) Int. Cl.
G06K 9/00 (2006.01)

(52) U.S. Cl. .................................................... 382/100
(58) Field of Classification Search ................. 382/100, 382/108–109, 199, 232, 305; 117/15, 68, 117/223; 356/30
See application file for complete search history.

(56) References Cited

U.S. PATENT DOCUMENTS

| 4,900,147 A | | 2/1990 | Bowley et al. ............... 356/30 |
|---|---|---|---|
| 5,013,531 A | * | 5/1991 | Snyder et al. ............... 117/223 |
| 5,076,698 A | | 12/1991 | Smith et al. ................. 356/376 |
| 5,124,935 A | | 6/1992 | Wallner et al. .............. 364/525 |
| 5,138,179 A | * | 8/1992 | Baba et al. ................... 117/15 |
| 5,193,685 A | | 3/1993 | Trevithick ................... 209/3.1 |
| 5,544,254 A | | 8/1996 | Hartley et al. .............. 382/108 |
| 5,548,661 A | * | 8/1996 | Price et al. ................. 382/133 |
| 6,174,365 B1 | * | 1/2001 | Sanjoh ........................ 117/68 |

FOREIGN PATENT DOCUMENTS

JP 06-170106 * 6/1994

OTHER PUBLICATIONS

Hannaford, et al. "Telerobotic Remote Handling of Protein Crystals", University of Washington, pp. 1–6, 1996.*

(Continued)

Primary Examiner—Daniel Miriam

(57) ABSTRACT

A system utilizing a digital computer for acquiring, storing and evaluating crystal images. The system includes a video camera (12) which produces a digital output signal representative of a crystal specimen positioned within its focal window (16). The digitized output from the camera (12) is then stored on data storage media (32) together with other parameters inputted by a technician and relevant to the crystal specimen. Preferably, the digitized images are stored on removable media (32) while the parameters for different crystal specimens are maintained in a database (40) with indices to the digitized optical images on the other data storage media (32). Computer software is then utilized to identify not only the presence and number of crystals and the edges of the crystal specimens from the optical image, but to also rate the crystal specimens by various parameters, such as edge straightness, polygon formation, aspect ratio, surface clarity, crystal cracks and other defects or lack thereof, and other parameters relevant to the quality of the crystals.

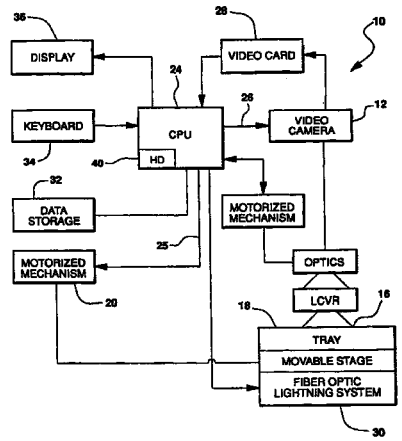

OTHER PUBLICATIONS

Gilliland, et al. "Screening for Crystallization Conditions and Robotics", International Union of Crystallography, pp. 408–413, 1994.*

Ward et al. "Automatic Preparation of Protein Crystals Using Laboratory Robotics and Automated Visual Inspection", Journal of Crystal Growth 90 (1988) 325–339.

Zuk et al. "Video Monitoring and Analysis subsystem: A CCD–Based Monitoring System for the Protein Crystal Growth Apparatus", SPIE vol. 1118, (1989) 154–159.

Sawyer et al. "Crystal Surface Analysis Using Matrix Textural Features Classified by a Probabilistic Neural Network", SPIE vol. 1567 (1991) 254–263.

Zuk et al. "Methods of analysis of protein crystal images", Journal of Crystal Growth 110 (91991) 148–155.

Koszelak et al. "Protein crystal growth rates determined by time lapse microphotography", Journal of Crystal Growth 110 (1991) 177–181.

Vogels et al. "Real time digital video image processing of in situ crystal growth", Journal of Crystal Growth 114 (1991) 239–248.

Schumann et al. "The Use of a Video Cameral and PC for Crystal Image Analysis", Proceedings of The South African Sugar Technologists' Assocation (Jun. 1993) 135–139.

* cited by examiner

US 6,529,612 C1

EX PARTE
REEXAMINATION CERTIFICATE
ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 5–6 and 9 is confirmed.

Claims 1 and 8 are determined to be patentable as amended.

Claims 2–4 and 7, dependent on an amended claim, are determined to be patentable.

New claims 10–48 are added and determined to be patentable.

1. A system for utilizing a digital computer to evaluate microscopic details of at least one *protein* crystal, comprising:
   a camera which generates an output signal representative of an image positioned in a focal plane of the camera,
   a tray which positions said at least one *protein* crystal in said focal plane,
   a computer processing unit having a persistent storage device, which computer processing unit acquires said output signal from said camera,
   said computer processing unit being programmed to evaluate said stored image from said camera and for generating a result signal representative thereof,
   said computer processing unit being programmed to store said result signals in said persistent storage device and performing at least one function selected from the group consisting of: [to count crystals,] to generate three-dimensional surface plots of *protein* crystals within a database, and to determine crystal size by determination of the length of the perimeter of said *protein* crystals *through simulating missing edges*.

8. A system for utilizing a digital computer to evaluate microscopic details of at least one *protein* crystal, comprising:
   a camera which generates an output signal representative of an image positioned in a focal plane of the camera,
   a tray which positions said at least one *protein* crystal in said focal plane,
   a computer processing unit having a persistent storage device, which computer processing unit acquires said output signal from said camera,
   said computer processing unit being programmed to evalute said stored image from said camera and for generating a result signal representative thereof,
   said computer processing unit being programmed to store said result signals in said persistent storage device *and performing at least one function selected from the group consisting of: to generate three-dimensional surface plots of protein crystals within a database, and to determine crystal size by determination of the length of the perimeter of said protein crystals through simulating missing edges*, and an optical fiber extending [between] *from* a light source *producing light, the light directed through said optical fiber* onto said at least one *protein* crystal [and said at least one crystal].

*10. A system for utilizing a digital compter to evaluate microscopic details of at least one protein crystal, comprising:*
   *a camera which generates an output signal representative of an image positioned in a focal plane of the camera,*
   *a tray which positions said at least one protein crystal in said focal plane, a computer processing unit having a persistent storage device, which computer processing unit acquires said output signal from said camera, said computer processing unit being programmed to evaluate said stored image from said camera and for generating a result signal representative thereof, said computer processing unit being programmed to store said result signals in said persistent storage device and performing at least one function selected from the group consisting of: to generate three-dimensional surface plots of protein crystals within a database, and to determine crystal size by determination of the length of the perimeter of said protein crystals throught simulation of missing edges, and comprising a movable stage for automatically positioning said at least one protein crystal in said focal plane, wherein data relating to said at least one protein crystal is stored in the database.*

*11. A system for utilizing a digital computer to evaluate microscopic details of at least one protein crystal, comprising:*
   *a camera which generates an output signal representative of an image positioned in a focal plane of the camera, a tray which positions said at least one protein crystal in said focal plane, a computer processing unit having a persistent storage device, which computer processing unit acquires said output signal from said camera, said computer processing unit being programmed to evaluate said stored image from said camera and for generating a result signal representative thereof, said computer processing unit being programmed to store said result signals in said persistent storage device and performing at least one function selected from the group consisting of: to generate three-dimensional surface plots of protein crystals within a database, and to determine protein crystal size by determination of the length of the perimeter of said protein crystals through simulation of missing edges, wherein data relating to said at least one protein crystal is stored in the database, and comprising a computer algorithm executed by said computer processing unit for rating said at least one protein crystal with respect to predetermined standards.*

*12. A system for utilizing a digital computer to evaluate microscopic details of at least one crystal, comprising:*
   *a camera which generates an output signal representative of an image positioned in a focal plane of the camera, a tray which positions said at least one protein crystal in said focal plane, a computer processing unit having a persistent storage device, which computer processing unit acquires said output signal from said camera, said computer processing unit being programmed to evaluate said stored image from said camera and for generating a result signal representative thereof, said computer processing unit being programmed to store* said result signals in said persistent storage device and performing at least one function selected from the group consisting of: to generate three-dimensional surface plots of protein crystals within a database, and to determine crystal size by determination of the length of the perimeter of said protein crystals through simulating missing edges, and comprising a movable stage for automatically positioning said at least one crystal in said focal plane, and comprising a computer algorithm executed by said computer processing unit for rating said at least one crystal with respect to predetermined standards.

13. A system for utilizing a digital computer to evaluate microscopic details of at least one crystal, comprising:

a camera which generates an output signal representative of an image positioned in a focal plane of the camera, a tray which positions said at least one crystal in said focal plane, a computer processing unit having a persistent storage device, which computer processing unit acquires said output signal from said camera, said computer processing unit being programmed to evaluate said stored image from said camera and for generating a result signal representative thereof, said computer processing unit being programmed to store said result signals in said persistent storage device, and a T-squared filter to identify said at least one crystal where said T-squared filter comprises a software program executed by said computer processing unit, wherein said computer processing unit generates output signals to control the movement of said movable stage.

14. A system for utilizing a digital computer to evaluate microscopic details of at least one crystal, comprising:

a camera which generates an output signal representative of an image positioned in a focal plane of the camera, a tray which positions said at least one crystal in said focal plane, a computer processing unit having a persistent storage device, which computer processing unit acquires said output signal from said camera, said computer processing unit being programmed to evaluate said stored image from said camera and for generating a result signal representative thereof, said computer processing unit being programmed to store said result signals in said persistent storage device and performing at least one function selected from the group consisting of: to generate three-dimensional surface plots of protein crystals within a database, and to determine crystal size by determination of the length of the perimeter of said protein crystals through simulating missing edges, and an optical fiber extending from a light source producing light, the light directed through said optical fiber onto said at least one protein crystal, and comprising a movable stage for automatically positioning said at least one protein crystal in said focal plane.

15. A system for utilizing a digital computer to evaluate microscopic details of at least one crystal comprising:

a camera which generates an output signal representative of an image positioned in a focal plane of the camera, a tray which positions said at least one crystal in said focal plane, a computer processing unit having a persistent storage device, which computer processing unit acquires said output signal from said camera, said computer processing unit being programmed to evaluate said stored image from said camera and for generating a result signal representative thereof, said computer processing unit being programmed to store said result signals in said persistent storage device, and an optical fiber extending from a light source producing light, the light directed through said optical fiber onto said at least one crystal, and comprising a computer algorithm executed by said computer processing unit for scoring said at least one crystal with respect to predetermined standards of examination and evaluation of the straightness of crystal edges, defects in said at least one crystals, or fractures in said at least one crystal.

16. A system for utilizing a digital computer to evaluate microscopic details of at least one crystal, comprising:

a camera which generates an output signal representative of an image positioned in a focal plane of the camera, a tray which positions said at least one crystal in said focal plane, a computer processing unit having a persistent storage device, which computer processing unit acquires said output signal from said camera, said computer processing unit being programmed to evaluate said stored image from said camera and for generating a result signal representative thereof, said computer processing unit being programmed to store said result signals in said persistent storage device, and a computer algorithm executed by said computer processing unit for simulating edges of crystals missing in said image generated by said camera, and comprising a movable stage for automatically positioning said at least one crystal in said focal plane.

17. A system for utilizing a digital computer to evaluate microscopic details of a protein crystallization specimen residing on a crystallization media comprising:

a video camera which generates a digital output signal representative of the specimen in a focal plane of said camera; a motor coupled to at least one of: a specimen stage and said camera for automatically positioning the specimen within the focal plane of said camera; a database for acquiring and storing said output signal from said camera; and a computational algorithm for evaluating said stored output signal from said camera and for generating a result signal representative of a specimen condition and performing at least one function selected from the group consisting of: to generate three-dimensional surface plots of protein crystals within a database, and to determine crystal size by determination of the length of the perimeter of said protein crystals through simulating missing edges.

18. The system of claim 17 further comprising a centering algorithm coupled to said motor for converging a central region of the specimen with a central region of the camera focal plane.

19. The system of claim 18 wherein said centering algorithm operates automatically.

20. The system of claim 17 further comprising a drop identification algorithm for evaluating a liquid drop associated with the specimen.

21. The system of claim 17 wherein said motor is coupled to said camera.

22. The system of claim 17 wherein said database also stores crystal relevant parameters.

23. The system of claim 22 wherein said crystal relevant parameters include at least one parameter of the group consisting of: crystal specimen pH, crystal specimen temperature, crystal specimen protein type, detergents present, additives present, preservatives present, reservoir buffer present, reservoir buffer concentration, reservoir buffer pH, crystal specimen volume, notes, crystal specimen score, and crystal specimen drop descriptor.

24. The system of claim 22 wherein said database is relational between said output signal and said crystal parameters.

25. The system of claim 17 wherein the specimen condition relates to crystallization quality.

26. The system of claim 17 wherein said result signal is classified into a preselected plurality of states.

27. A process for analyzing crystal growth comprising the steps of:
adjusting the position of a crystal growth experiment relative to a video camera such that said experiment is within a focal window of the video camera;
generating an output signal from said video camera, said signal representing an image of said experiment;
acquiring said output signal in a processing unit;
storing said output signal in a first data storage device;
inputting a crystal relevant parameter to said processing unit;
storing said crystal relevant parameter to a second data storage device; and
correlating said crystal relevant parameter and said output signal stored within said first data storage device with an index or a pointer.

28. The process of claim 27 wherein said experiment is positioned within the focal window of said video camera by a movable stage driven by a motorized mechanism.

29. The process of claim 28 wherein said stage supports a plurality of experiments.

30. The process of claim 27 wherein said experiment is positioned within the focal window of said video camera by movable camera.

31. The process of claim 27 wherein adjustment relative to the focal plane is under activation control of said processing unit.

32. The process of claim 27 further comprising the step of illuminating said experiment.

33. The process of claim 32 wherein the illumination is reflective lighting.

34. The process of claim 32 further comprising the step of controlling a lighting parameter selected from the group consisting of: intensity, presence of light, and angle of polarization.

35. The process of claim 34 wherein controlling the lighting parameter is through the use of a control unit.

36. The process of claim 27 wherein said data storage device is a removable data storage medium.

37. The process of claim 27 wherein said first data storage device and said second data storage device are the same device.

38. The process of claim 27 further comprising the step of digitally filtering said output signal prior to storing said output signal.

39. The process of claim 27 wherein said crystal relevant parameters include at least one parameter of the group consisting of: crystal specimen pH, crystal specimen temperature, crystal specimen protein type, detergents present, additives present, perservatives present, reservoir buffer present, reservoir buffer concentration, reservoir buffer pH, crystal specimen volume, notes, crystal specimen score, and crystal specimen drop descriptor.

40. The process of claim 27 further comprising the step of scoring said output image as a crystal image score.

41. The process of claim 40 further comprising technician entry of information.

42. The process of claim 40 further comprising storing said crystal image score as part of said crystal relevant parameters.

43. A crystal growth analysis obtained by the process of claim 27.

44. The process of claim 27 further comprising performing at least one function selected from the group consisting of: crystal counting, generating three-dimensional surface plots from said output signal stored within said database, and preparing a plot as a function of time from a plurality of said output signal collected for the specimen as a function of time.

45. A process for analyzing crystal growth comprising the steps of:
adjusting the position of a crystal growth experiment relative to a video camera such that said experiment is within a focal window of the video camera;
generating an output signal from said video camera, said signal representing an image of said experiment;
acquiring said output signal in a processing unit;
storing said output signal in a first data storage device;
inputting a crystal relevant parameter to said processing unit;
storing said crystal relevant parameter to a second data storage device;
correlating said crystal relevant parameter and said output signal stored within said first data storage device with an index or a pointer; and
data compressing said output signal prior to storing said output signal.

46. A process for analyzing crystal growth comprising the steps of:
adjusting the position of a crystal growth experiment relative to a video camera such that said experiment is within a focal window of the video camera;
generating an output signal from said video camera, said signal representing an image of said experiment;
acquiring said output signal in a processing unit;
storing said output signal in a first data storage device;
inputting a crystal relevant parameter to said processing unit;
storing said crystal relevant parameter to a second data storage device; and
correlating said crystal relevant parameter and said output signal stored within said first data storage device with an index or a pointer;
wherein said crystal relevant parameters are input into a template.

47. A process for analyzing crystal growth comprising the steps of:
adjusting the position of a crystal growth experiment relative to a video camera such that said experiment is within a focal window of the video camera;
generating an output signal from said video camera, said signal representing an image of said experiment;
acquiring said output signal in a processing unit;
storing said output signal in a first data storage device;
inputting a crystal relevant parameter to said processing unit;
storing said crystal relevant parameter to a second data storage device;

correlating said crystal relevant parameter and said output signal stored within said first data storage device with an index or a pointer; and scoring said output image as a crystal image score, wherein scoring comprises the steps of:
T-square filtering said output image;
low pass filtering said output image;
digitally filling image gaps in said output signal; and
assigning said crystal image score.

48. *A process for analyzing crystal growth comprising the steps of:*

*adjusting the position of a crystal growth experiment relative to a video camera such that said experiment is within a focal window of the video camera;*

*generating an output signal from said video camera, said signal representing an image of said experiment;*

*acquiring said output signal in a processing unit;*

*storing said output signal in a first data storage device;*

*inputting a crystal relevant parameter to said processing unit;*

*storing said crystal relevant parameter to a second data storage device;*

*correlating said crystal relevant parameter and said output signal stored within said first data storage device with an index or a pointer; and*

*scoring said output image as a crystal image score, wherein said crystal image score is determined based on a condition selected from the group consisting of: crystal edge straightness, crystal defects, crystal fractures, protein crystal count, crystal perimeter symmetry, crystal perimeter roughness, and center of gravity.*

\* \* \* \* \*